(12) United States Patent
Lange

(10) Patent No.: US 8,591,549 B2
(45) Date of Patent: Nov. 26, 2013

(54) VARIABLE DUROMETER LUMBAR-SACRAL IMPLANT

(75) Inventor: Eric C. Lange, Pleasanton, CA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 140 days.

(21) Appl. No.: 13/082,946

(22) Filed: Apr. 8, 2011

(65) Prior Publication Data
US 2012/0259364 A1 Oct. 11, 2012

(51) Int. Cl.
*A61B 17/70* (2006.01)

(52) U.S. Cl.
USPC ........................................................ 606/249

(58) Field of Classification Search
USPC .................... 606/246–249; 623/17.11–17.16
See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

"Dispositivo Intervertebrale Ammortizzante DIAM," date unknown, p. 1.

(Continued)

*Primary Examiner* — Jan Christopher Merene
*Assistant Examiner* — Steven Cotroneo (57) ABSTRACT

Medical devices for the treatment of spinal conditions are described herein. The medical device includes a main body that is adapted to be placed between the L5 vertebra and the sacrum so that the main body acts as a spacer with respect to the L5 vertebra and the sacrum to maintain distraction therebetween when the spine moves in extension. The main body is formed from a material having a gradual variation in modulus.

20 Claims, 8 Drawing Sheets

(56) References Cited

U.S. PATENT DOCUMENTS

| | | |
|---|---|---|
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,165 A | 3/1991 | Watanabe |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,133,717 A | 7/1992 | Chopin |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,659 A | 5/1995 | Lee et al. |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,990 B1 | 2/2003 | Ray |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1* | 9/2003 | Taylor .................. 623/17.16 |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |

(56) References Cited

U.S. PATENT DOCUMENTS

| | | |
|---|---|---|
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 * | 7/2007 | Le Couedic et al. ........ 623/17.11 |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartman et al. |
| 7,862,615 B2 | 1/2011 | Carli et al. |
| 7,901,430 B2 | 3/2011 | Matsuura et al. |
| 8,083,795 B2 * | 12/2011 | Lange et al. ................ 623/17.11 |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 * | 6/2004 | Le Couedic et al. ........ 623/17.11 |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 * | 6/2006 | Taylor ........................ 623/17.13 |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 * | 1/2007 | Anderson et al. ............... 606/61 |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 * | 7/2007 | Dewey et al. ................... 606/61 |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |

(56) References Cited

U.S. PATENT DOCUMENTS

| | | |
|---|---|---|
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0140082 A1 | 6/2008 | Erdem et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0099610 A1 | 4/2009 | Johnson et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1* | 9/2009 | Carls et al. ............ 606/246 |
| 2009/0270918 A1 | 10/2009 | Attia et al. |
| 2009/0326538 A1 | 12/2009 | Sennett et al. |
| 2010/0121379 A1 | 5/2010 | Edmond |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |
| 2012/0259366 A1* | 10/2012 | Lange ............ 606/248 |

FOREIGN PATENT DOCUMENTS

| | | |
|---|---|---|
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| FR | 2884135 | 4/2005 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | 2006110578 | 10/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Discord Tech., 2006, vol. 00, No. 00, pp. 1-7.

Benzel et al., "Posterior Cervical Interspinous Compression Wiring and Fusion for Mid to Low Cervical Spinal Injuries," J. Neurosurg., Jun. 1989, pp. 893-899, vol. 70.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

(56) References Cited

OTHER PUBLICATIONS

Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Kramer et al., "Intervetertebral Disk Diseases: Causes, Diagnosis, Treatment and Prophylaxis," pp. 244-249, Medical, 1990.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," Spine, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Phillips et al., "Biomechanics of Posterior Dynamic Stabiling Device (DIAM) After Facetectomy and Disectomy," The Spine Journal, 2006, vol. 6, pp. 714-722.
Porter, "Spinal Stenosis and Neurogenic Claudication," Spine, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," Spine, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," Spine, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopedique, 1988, pp. 15-22.
Senegas et al., "Stabilisation Lombaire Souple," Instabilitè Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrodèse," La Revue de Medécine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Sulzer Innotec, "DIAM—Modified CAD Geometry and Meshing," date unknown.
Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.
Taylor et al., "Device for Intervertebral Assisted Motion: Technique and Intial Results," 22 Neurosurg. Focus, Jan. 2007, vol. 22, No. 1, pp. 1-6.
Taylor et al., "Surgical Requirement for the Posterior Control of the Rotational Centers," date unknown.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.
Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.
Taylor, "Posterior Dynamic Stabilization using the DIAM (Device for Intervertebral Assisted Motion)," date unknown, pp. 1-5.
Taylor, "Présentation à un an d'un dispositif amortissant d'assistance discale," 5èmes journées Avances & Controverses en pathologie rachidienne, Oct. 1-2, 1998, Faculté Libre de Médecine de Lille.
Tsuji et al., "Ceramic Interspinous Block (CISB) Assisted Anterior Interbody Fusion," J. Spinal Disorders, 1990, pp. 77-86, vol. 3, No. 1.
Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.
Voydeville et al., "Experimental Lumbar Instability and Artificial Ligament," Eur. J. Orthop. Surg. Traumatol., Jul. 15, 2000, pp. 167-176, vol. 10.
Voydeville et al., "Lumbar Instability Treated by Intervertebral Ligamentoplasty with Smooth Wedges," Orthopédie Traumatologie, 1992, pp. 259-264, vol. 2, No. 4.
Waldemar Link, "Spinal Surgery: Instrumentation and Implants for Spinal Surgery," 1981, Link America Inc., New Jersey.
Wilke et al., "Biomedical Effect of Different Lumbar Interspinous Implants on Flexibilty and Intradiscal Pressure," Eur Spine J., Vo. 17, published online Jun. 27, 2008, pp. 1049-1056.
Wiltse et al., "The Treatment of Spinal Stenosis," Clinical Orthopaedics and Related Research, Urist, ed., Mar.-Apr. 1976, pp. 83-91, No. 115.

(56) References Cited

OTHER PUBLICATIONS

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," Spine, 1991, pp. S298-S301, vol. 16, No. 6, Supplement.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

Zucherman et al., "Clinical Efficacy of Spinal Instrumentation in Lumbar Degenerative Disc Disease," Spine, Jul. 1992, pp. 834-837, vol. 17, No. 7.

Wittenberg et al., "Flexibility and Distraction after Monosegmental and Bisegmental Lumbrosacral Fixation with Angular Stable Fixators," Spine, 1995, pp. 1227-1232, vol. 20, No. 11.

* cited by examiner

VARIABLE DUROMETER LUMBAR-SACRAL IMPLANT

BACKGROUND

This invention relates generally to devices for the treatment of spinal conditions, and more particularly, to the treatment of various spinal conditions that cause back pain. Even more particularly, this invention relates to devices that may be placed between adjacent spinous processes to treat various spinal conditions. For example, spinal conditions that may be treated with these devices may include spinal stenosis degenerative disc disease (DDD), disc herniations and spinal instability, among others.

The clinical syndrome of neurogenic intermittent claudication due to lumbar spinal stenosis is a frequent source of pain in the lower back and extremities, leading to impaired walking, and causing other forms of disability in the elderly. Although the incidence and prevalence of symptomatic lumbar spinal stenosis have not been established, this condition is the most frequent indication of spinal surgery in patients older than 65 years of age.

Lumbar spinal stenosis is a condition of the spine characterized by a narrowing of the lumbar spinal canal. With spinal stenosis, the spinal canal narrows and pinches the spinal cord and nerves, causing pain in the back and legs. It is estimated that approximately 5 in 10000 people develop lumbar spinal stenosis each year. For patients who seek the aid of a physician for back pain, approximately 12%-15% are diagnosed as having lumbar spinal stenosis.

Common treatments for lumbar spinal stenosis include physical therapy (including changes in posture), medication, and occasionally surgery. Changes in posture and physical therapy may be effective in flexing the spine to decompress and enlarge the space available to the spinal cord and nerves—thus relieving pressure on pinched nerves. Medications such as NSAIDS and other anti-inflammatory medications are often used to alleviate pain, although they are not typically effective at addressing spinal compression, which is the cause of the pain.

Surgical treatments are more aggressive than medication or physical therapy, and in appropriate cases surgery may be the best way to achieve lessening of the symptoms of lumbar spinal stenosis and other spinal conditions. The principal goal of surgery to treat lumbar spinal stenosis is to decompress the central spinal canal and the neural foramina, creating more space and eliminating pressure on the spinal nerve roots. The most common surgery for treatment of lumbar spinal stenosis is direct decompression via a laminectomy and partial facetectomy. In this procedure, the patient is given a general anesthesia and an incision is made in the patient to access the spine. The lamina of one or more vertebrae may be partially or completely removed to create more space for the nerves. The success rate of decompressive laminectomy has been reported to be in excess of 65%. A significant reduction of the symptoms of lumbar spinal stenosis is also achieved in many of these cases.

The failures associated with a decompressive laminectomy may be related to postoperative iatrogenic spinal instability. To limit the effect of iatrogenic instability, fixation and fusion may also be performed in association with the decompression. In such a case, the intervertebral disc may be removed, and the adjacent vertebrae may be fused. A discectomy may also be performed to treat DDD and disc herniations. In such a case, a spinal fusion would be required to treat the resulting vertebral instability. Spinal fusion is also traditionally accepted as the standard surgical treatment for lumbar instability. However, spinal fusion sacrifices normal spinal motion and may result in increased surgical complications. It is also believed that fusion to treat various spinal conditions may increase the biomechanical stresses imposed on the adjacent segments. The resultant altered kinematics at the adjacent segments may lead to accelerated degeneration of these segments.

As an alternative or complement to the surgical treatments described above, an interspinous process device may be implanted between adjacent spinous processes of adjacent vertebrae. The purposes of these devices are to provide stabilization after decompression, to restore foraminal height, and to unload the facet joints. They also allow for the preservation of a range of motion in the adjacent vertebral segments, thus avoiding or limiting possible overloading and early degeneration of the adjacent segments as induced by fusion. The vertebrae may or may not be distracted before the device is implanted therebetween. An example of such a device is the interspinous prosthesis described in U.S. Pat. No. 6,626,944, the entire contents of which are expressly incorporated herein by reference. This device, commercially known as the DIAM® spinal stabilization system, is designed to restabilize the vertebral segments as a result of various surgical procedures or as a treatment of various spinal conditions. It limits extension and may act as a shock absorber, since it provides compressibility between the adjacent vertebrae, to decrease intradiscal pressure and reduce abnormal segmental motion and alignment. This device provides stability in all directions and maintains the desired separation between the vertebral segments all while allowing motion in the treated segment.

Although currently available interspinous process devices typically work for their intended purposes, they could be improved. For example, where the spacer portion of the implant is formed from a hard material to maintain distraction between adjacent vertebrae, point loading of the spinous process can occur due to the high concentration of stresses at the point where the hard material of the spacer contacts the spinous process. This may result in excessive subsidence of the spacer into the spinous process. In addition, if the spinous process is osteoporotic, there is a risk that the spinous process could fracture when the spine is in extension. In addition, because of the human anatomy and the complex biomechanics of the spine, some currently available interspinous process devices may not be easily implantable in certain locations in the spine.

The spine is divided into regions that include the cervical, thoracic, lumbar, and sacrococcygeal regions. The cervical region includes the top seven vertebrae indentified as C1-C7. The thoracic region includes the next twelve vertebrae identified as T1-T12. The lumbar region includes five vertebrae L1-L5. The sacrococcygeal region includes five fused vertebrae comprising the sacrum. These five fused vertebrae are identified as the S1-S5 vertebrae. Four or five rudimentary members form the coccyx.

The sacrum is shaped like an inverted triangle with the base at the top. The sacrum acts as a wedge between the two iliac bones of the pelvis and transmits the axial loading forces of the spine to the pelvis and lower extremities. The sacrum is rotated anteriorly with the superior endplate of the first sacral vertebra angled from about 30 degrees to about 60 degrees in the horizontal plane. The S1 vertebra includes a spinous process aligned along a ridge called the medial sacral crest. However, the spinous process on the S1 vertebrae may not be well defined, or may be non-existent, and therefore may not be adequate for supporting an interspinous process device positioned between the L5 and S1 spinous processes.

Thus, a need exists for an interspinous process device that may be readily positioned between the L5 and S1 spinous processes. Moreover, there is a need to provide an interspinous process device that can provide dynamic stabilization to the instrumented motion segment and not affect adjacent segment kinematics.

SUMMARY

A spinal implant is described herein that is particularly adapted for placement between the spinous processes of the L5 vertebra and the S1 vertebra to provide dynamic stabilization. The implant includes an upper saddle defined by a pair of sidewalls joined by a bottom wall. The upper saddle sidewalls may flare slightly outwardly away from the sagittal plane toward the top of the implant while the bottom wall of the upper saddle may be concavely curved. In addition, the surfaces forming the upper saddle sidewalls and the upper saddle bottom wall extend in a direction, from the front of the implant to the rear of the implant, which is generally parallel to the sagittal plane. The upper saddle is configured to receive and support the spinous process of the L5 vertebra therein. The implant also includes a lower saddle defined by a pair of sidewalls joined by a top wall. The lower saddle sidewalls flare outwardly away from the sagittal plane toward the bottom of the implant. In addition, the surfaces forming the lower saddle sidewalls extend in a direction, from the front of the implant to the rear of the implant, outwardly away from the sagittal plane. The lower saddle top wall may be concavely curved. In addition, the surface forming the lower saddle top wall extends in a direction, from the front of the implant to the rear of the implant, toward the top of the implant. The lower saddle is not intended to engage and is not supported by the spinous process of the S1 vertebra. Rather the lower saddle merely provides a space into which that spinous process may extend when the implant is properly located in place.

The spinal implant described herein has outer sidewalls that extend on either side of the implant from the upper portion of the implant to the lower portion of the implant. The outer sidewalls flare outwardly away from the sagittal plane from the upper portion of the implant to give the implant a generally triangular-like shape. The wider bottom portion of the implant allows two lower lobes to be defined along the bottom portion of the implant adjacent to either side of the lower saddle. The lower lobes each define a channel extending through the thickness of the implant. The channels allow a fixation device to extend therethrough to fix the implant in the desired location. These channels flare outwardly so the fixation device can extend to the pedicles of the S1 vertebra. For example, the channels may extend at an angle of about 60 degrees away from the sagittal plane toward the rear of the implant and at an angle of about 5 degrees toward the top of the implant in a direction from the front of the implant toward the rear of the implant.

The spinal implant described herein may also define a passage that extends completely through the implant from one side of the implant to the other side of the implant. The passage may have a concavely curved trajectory when viewed from the top of the implant such that the openings on either side of the implant are generally aligned with a bottom portion of the upper saddle and the nadir of the passage is below and generally aligned along the sagittal plane with the lowest portion of the upper saddle bottom wall and the highest portion of the lower saddle top wall. A tether may extend through this passage. The curve of the passage facilitates a tether being threaded through the passage.

The spinal implant described herein may be formed as a unitary body of a polymeric material having a gradual variation in modulus along and/or across its cross-section. For example, the modulus may vary along the height of the body such that the upper portion of the body is more flexible than the lower portion of the body. Alternatively, the modulus may vary along the width of the body such that the outer lateral portions of the body are stiffer than the central portion of the body. The modulus may also vary along the width and height of the body such that the outer lateral portions and the lower portion of the body are stiffer than the central and upper portion of the body.

DETAILED DESCRIPTION

As used in this specification and the appended claims, the singular forms "a," "an" and "the" include plural referents unless the context clearly dictates otherwise. Thus, for example, the term "a member" is intended to mean a single member or a combination of members, and "a material" is intended to mean one or more materials, or a combination thereof. Furthermore, the words "proximal" and "distal" refer to directions closer to and away from, respectively, an operator (e.g., surgeon, physician, nurse, technician, etc.) who would insert the medical device into the patient, with the tip-end (i.e., distal end) of the device inserted inside a patient's body first. Thus, for example, the device end first inserted inside the patient's body would be the distal end of the device, while the device end last to enter the patient's body would be the proximal end of the device.

As used in this specification and the appended claims, the terms "upper", "top", "lower", "bottom", "front", "back", "rear", "left", "right", "side", "middle" and "center" refer to portions of or positions on the implant when the implant is oriented in its implanted position.

As used in this specification and the appended claims, the term "axial plane" when used in connection with particular relationships between various parts of the implant means a plane that divides the implant into upper and lower parts. As shown in the FIGS., the axial plane is defined by the X axis and the Z axis. As used in this specification and the appended claims, the term "coronal plane" when used in connection with particular relationships between various parts of the implant means a plane that divides the implant into front and back parts. As shown in the FIGS., the coronal plane is defined by the X axis and the Y axis. As used in this specification and the appended claims, the term "sagittal plane" when used in connection with particular relationships between various parts of the implant means a plane that divides the implant into left and right parts. As show in the FIGS., the sagittal plane is defined by the Y axis and the Z axis.

As used in this specification and the appended claims, the term "body" when used in connection with the location where the device of this invention is to be placed to treat spinal disorders, or to teach or practice implantation methods for the device, means a mammalian body. For example, a body can be a patient's body, or a cadaver, or a portion of a patient's body or a portion of a cadaver.

As used in this specification and the appended claims, the term "parallel" describes a relationship, given normal manufacturing or measurement or similar tolerances, between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e. t a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

As used in this specification and the appended claims, the terms "normal", "perpendicular" and "orthogonal" describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal, perpendicular or orthogonal to a curved surface when the line and the curved surface intersect at an angle of approximately 90 degrees within a plane. Two geometric constructions are described herein as being "normal", "perpendicular", "orthogonal" or "substantially normal", "substantially perpendicular", "substantially orthogonal" to each other when they are nominally 90 degrees to each other, such as for example, when they are 90 degrees to each other within a tolerance. Such tolerances can include, for example, manufacturing tolerances, measurement tolerances or the like.

A spinal implant 10 is described herein that is particularly adapted for placement between the spinous processes of the L5 vertebra and the S1 vertebra. However, it is to be understood that even though the following description of implant 10 is provided with reference to the L5 spinous process and the S1 spinous process, implant 10 may be used between other adjacent spinous process and the discussion of the L5 spinous process may be interpreted to include any superior spinous process and the S1 spinous process may be interpreted to include the adjacent inferior spinous process.

Figure 1:
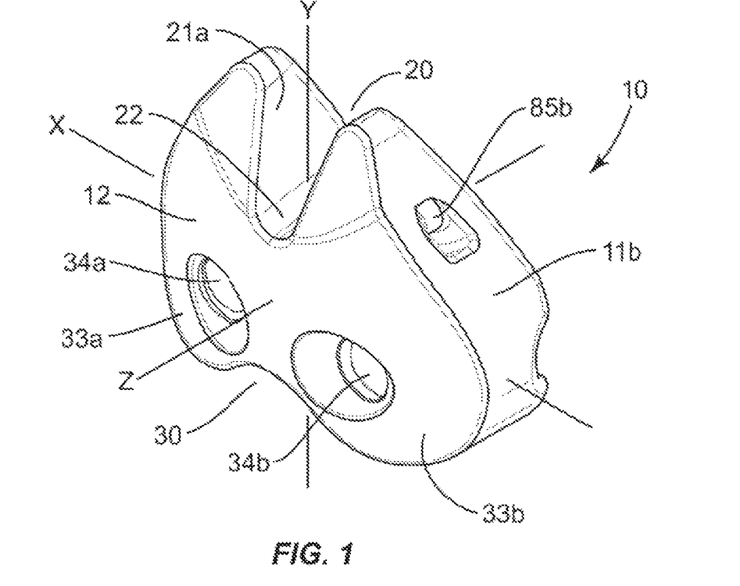
FIG. 1 is a front perspective view of one embodiment of a lumbar-sacral implant.
Figure 2:
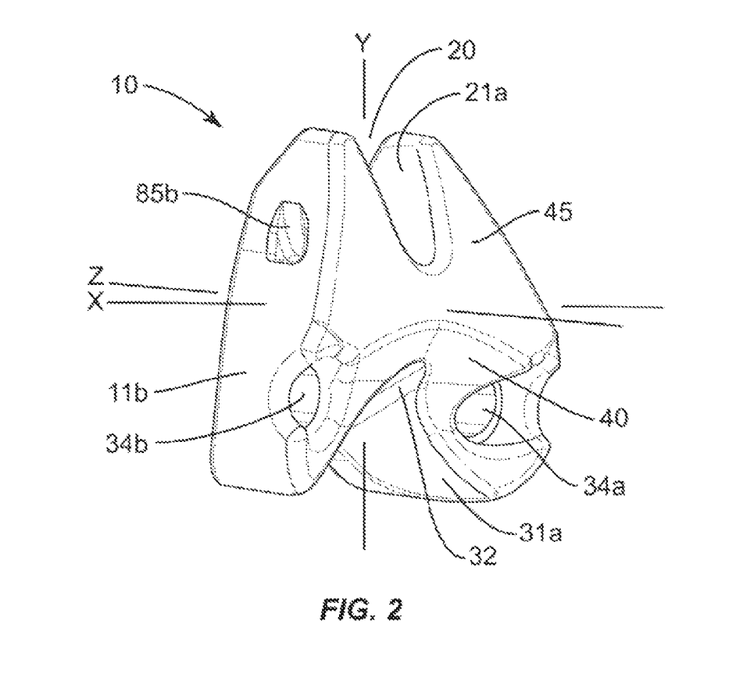
FIG. 2 is a rear perspective view of the embodiment of a lumbar-sacral implant shown in FIG. 1.
Figure 3:
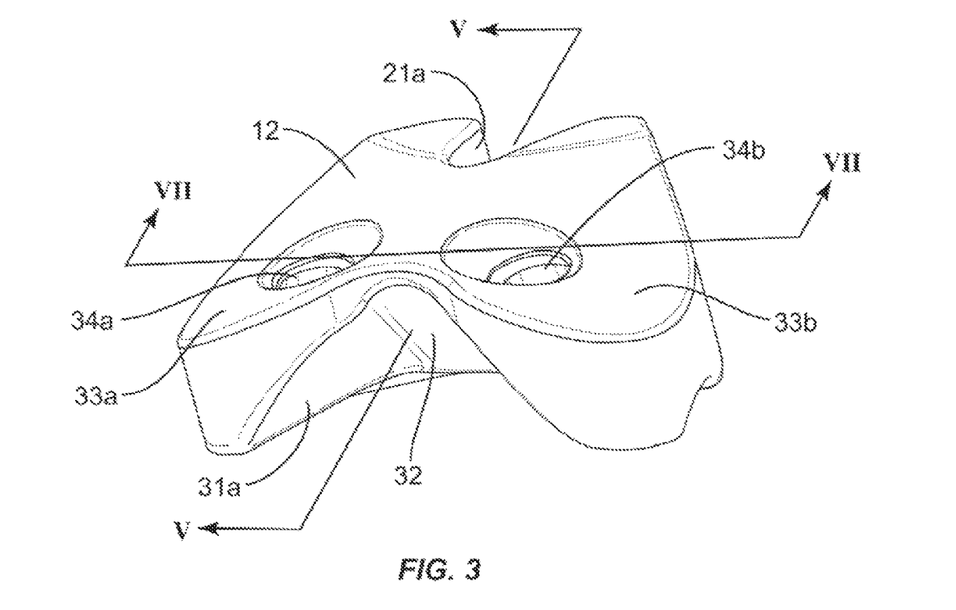
FIG. 3 is a bottom perspective view of the embodiment of a lumbar-sacral implant shown in FIG. 1.
Figure 4:
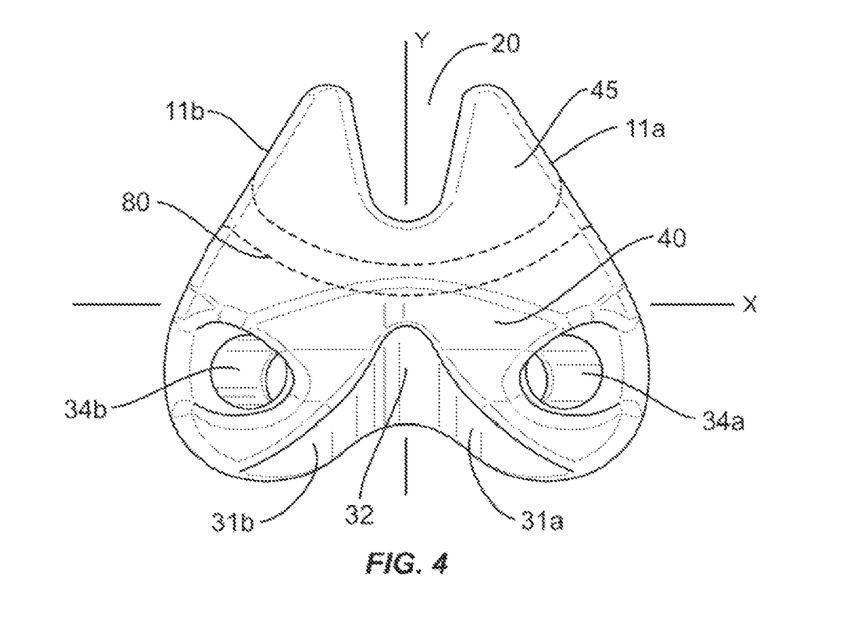
FIG. 4 is a rear elevation view of the embodiment of a lumbar-sacral implant shown in FIG. 1.
Figure 5:
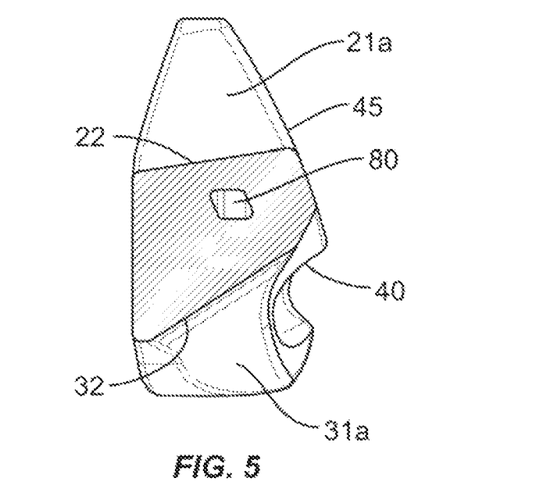
FIG. 5 is a cross-sectional view of the embodiment of a lumbar-sacral implant shown in FIG. 1 taken along line V-V in FIG. 3.
Figure 6:
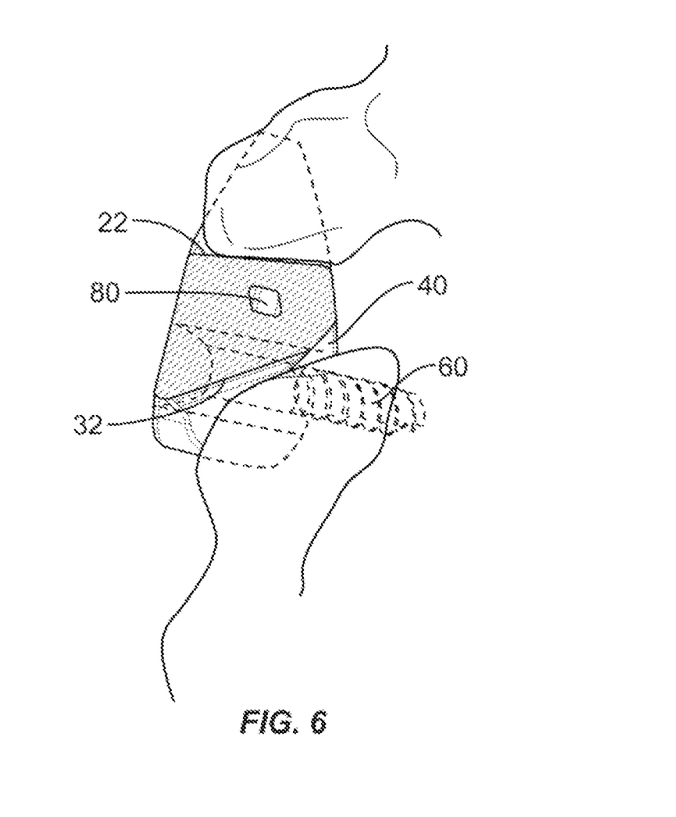
FIG. 6 is a cross-sectional view of the embodiment of a lumbar-sacral implant shown in FIG. 5 located between the L5 spinous process and the sacrum.
Figure 7:
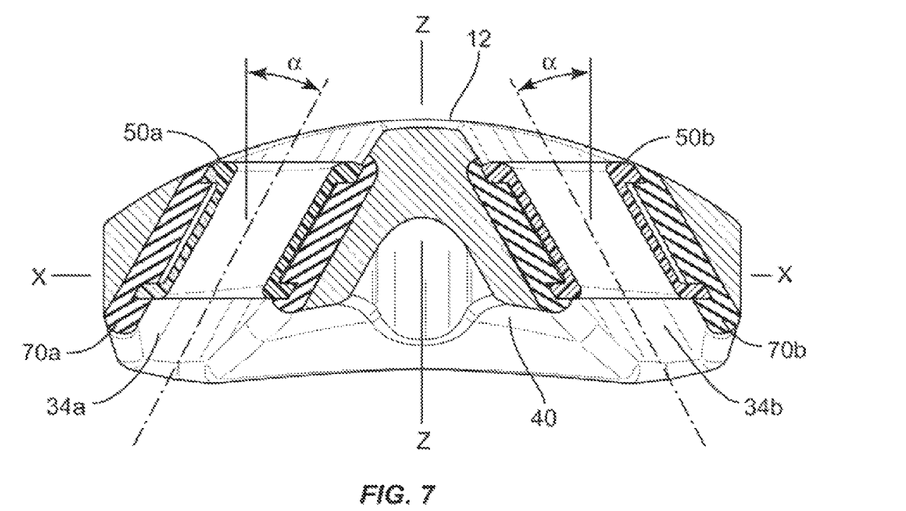
FIG. 7 is a cross-sectional view of the embodiment of a lumbar-sacral implant shown in FIG. 1 taken along line VII-VII FIG. 3.
Figure 7A:
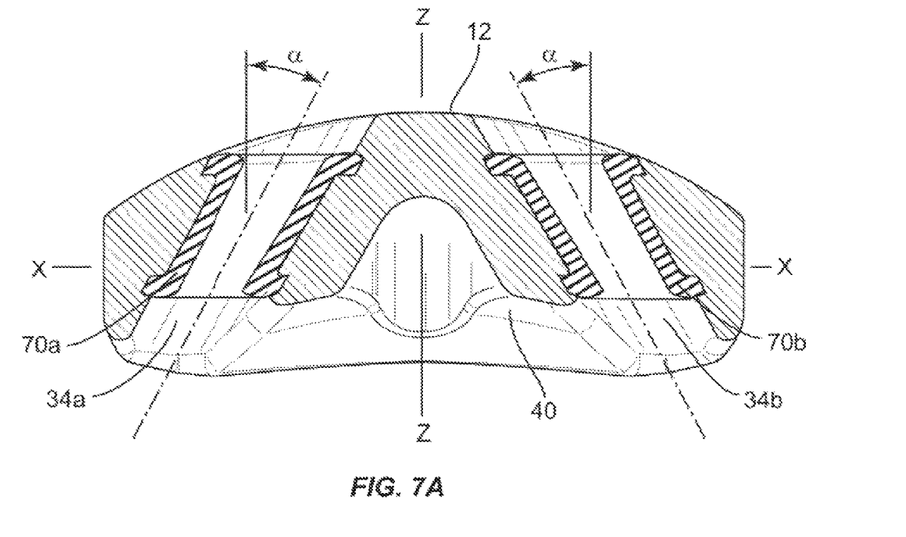
FIG. 7A is cross-sectional view similar to the view shown in FIG. 7 showing an alternate embodiment of the lumbar-sacral implant shown in FIG. 1.
Figure 8:
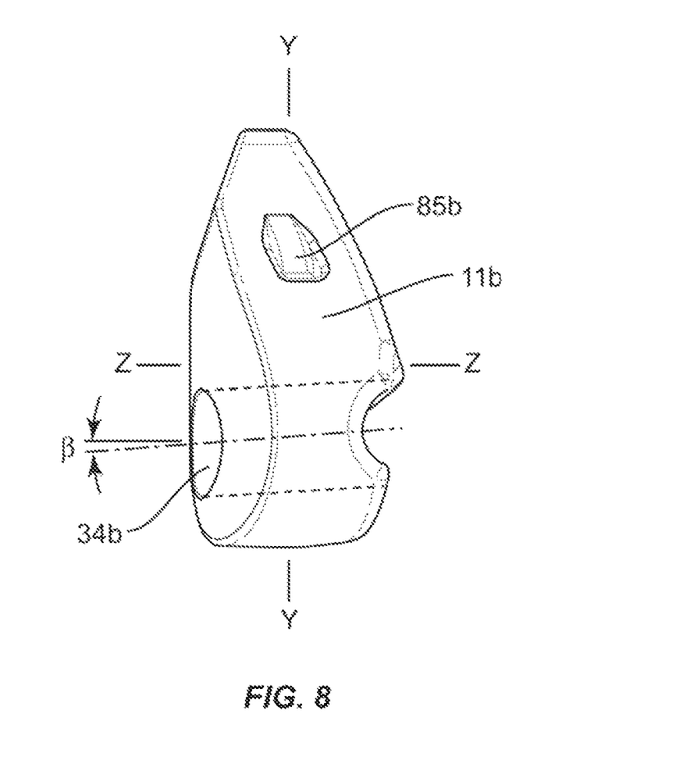
FIG. 8 is a side elevation view of the lumbar-sacral implant shown in FIG.

Implant 10 includes an upper saddle 20 defined by a pair of sidewalls 21a and 21b joined by a bottom wall 22. Upper saddle 20 receives and supports the spinous process of the L5 vertebra therein. Upper saddle sidewalls 21a and 21b may flare slightly outwardly away from the sagittal plane toward the top of implant 10 while upper saddle bottom wall 22 may be concavely curved. Implant 10 may have a variable radius (from about 3.0 mm on the ventral face 12 to about 2.0 mm on the dorsal face 45. This allows implant 10 to engage the L5 spinous process, which is usually thicker at the base. As shown in FIG. 5, upper saddle 20 may be oriented at about a 10 degree angle in the sagittal plane. The angle could be as large as about degrees. The surfaces forming upper saddle sidewalls 21a and 21b and upper saddle bottom wall 22 may be generally parallel to the sagittal plane. This configuration for upper saddle 20 allows upper saddle 20 to receive and support the spinous process of an L5 vertebra therein. The height of upper saddle sidewalls 21a and 21b should be chosen so that upper saddle sidewalls 21a and 21b prevent the upper portion of implant 10 from moving laterally out of engagement with the spinous process of the L5 vertebra. Upper saddle sidewalls 21a and 21b may extend between ⅓ and ½ of the base of the spinous process so they engage the lamina by about 2 to 3 mm. Upper saddle sidewalls 21a and 21b may not have a constant cross-section. This would allow upper saddle 20 to accommodate the variable thickness of the spinous process. Implant 10 also includes a lower saddle 30 defined by a pair of sidewalls 31a and 31b joined by a top wall 32. As described in more detail below, lower saddle 30 has a configuration to provide clearance of implant 10 over the S1 spinous process. As such, lower saddle 30 would not engage the spinous process of the S1 vertebra. Lower saddle sidewalls 31a, and 31b flare outwardly away from the sagittal plane toward the bottom of implant 10.

Upper saddle sidewalls 21a and 21b flare out and have a variable angle. The angle starts at about 40 degrees at the upper portion of upper saddle 20 and varies so that the angle is about 25 degrees at about the lowermost portion of upper saddle 20. Lower saddle sidewalls 31a and 31b flare out and have a constant angle between about 25 degrees and about 35 degrees. Lower saddle top wall 32 may be concavely curved or may have another configuration that allows the lower portion of implant 10 to be fixed to the S1 pedicles and minimizes any interference between the S1 spinous process and the rear of implant 10. Lower saddle top wall 32 is inclined between about 30 degrees and about 35 degrees in the sagittal plane.

Implant 10 has outer sidewalls 11a and 11b that extend on either side of implant 10 from the upper portion of implant 10 to the lower portion of implant 10. Outer sidewalls 11a and 11b flare outwardly away from the sagittal plane from the upper portion of implant 10 to give implant 10 a generally triangular shape. In addition, the overall shape of implant 10 transfers load from the L5 spinous process to the S1 pedicles instead of to the S1 spinous process or the S1 laminae. This is especially helpful where implant 10 is used in the L5-S1 level since the small size and shape of the S1 spinous process may not provide adequate support for an implant.

The front face 12 of implant 10 may have a curved profile that tapers from about 0 degrees along the middle of front face 12 to about 35 degrees adjacent to sidewalls 11a, 11b. Implant 10 may have a curvature radius of between about 20 mm and about 30 mm. The generally triangular shape, where the base is larger than the top results in a constant pressure applied along the cross-sectional area of implant 10. The shape of implant 10 also provides a better fit in the L5/S1 space and therefore offers stability for implant 10. The rear of implant 10 has a stepped configuration and includes a shelf 40 separating the rear of implant 10 into an upper portion and a lower portion. Shelf 40 may be curved and is located so it is generally aligned with or above channels 34a and 34b. Shelf 40 acts as a transition between the upper and lower portions of the rear of implant 10 and ensures that implant 10 will fit properly in the patient's anatomy. The upper rear portion of implant 10 is defined by the rear wall 45, which flares outwardly from the top of implant 10. Rear wall 45 is curved such that it does not compete for engagement with upper saddle 20 but rather allows implant 10 to rest freely on the L5 lamina. This allows for easy implantation on the L5 level. The thickness of implant 10 gradually increases from the top of implant 10 to shelf 40. This taper may be between about 30 degrees and about 50 degrees. The bottom rear portion of implant 10 has a thinner profile and provides clearance so that lower saddle 30 does not engage the inferior spinous process. This results in practically no load being transferred from implant 10 to the inferior spinous process. Indeed, lower saddle 30 may be configured such that it is spaced from and does not engage the inferior spinous process when implant 10 is implanted in the patient.

The wider bottom portion of implant 10 allows two lower lobes 33a and 33b to be defined along the bottom portion of implant 10 adjacent to either side of lower saddle 30 and provides an area through which implant 10 may be fixed to the spine. The wider bottom portion of implant 10, and indeed the overall configuration of implant 10, also allow implant 10 to withstand higher forces being placed on it and helps to ensure compression forces placed on implant 10 are evenly distributed throughout the body of implant 10.

Each lower lobe 33a and 33b defines a channel 34a and 34b extending through implant 10. Channels 34a and 34b allow a fixation device 60, such as a cortical screw or similar device, to extend therethrough to fix implant 10 in the desired location on the spine. As such, the internal diameter of channels 34a and 34b should be sufficient to allow passage of fixation device 60 therethrough, but should not be so large as to allow too much "play", or too big of a gap, between fixation device 60 and channels 34a and 34b. For example, channels 34a and 34b could have an internal diameter that is about 0.5 mm to about 1 mm greater than the outer diameter of fixation device 60. Channels 34a and 34b flare outwardly from about the mid-line of implant 10 and adjacent to the top of the bottom portion of implant 10 so that fixation device 60 can be located therein and extend to the pedicles of the S1 vertebra. For example, channels 34a and 34b may extend at an angle α of about 60 degrees away from the sagittal plane toward the rear of implant and at an angle β of about 5 degrees toward the top of implant 10 in a direction from the front of implant 10 toward the rear of implant 10. Alternatively, angle α could be between about 45 degrees and about 60 degrees, while angle β could be between about 5 degrees and about 10 degrees. The wider bottom portion of implant 10, and indeed the overall configuration of implant 10, also allow implant 10 to withstand higher forces being placed on it and helps to ensure compression forces placed on implant 10 are evenly distributed throughout the body of implant 10.

Figure 9:
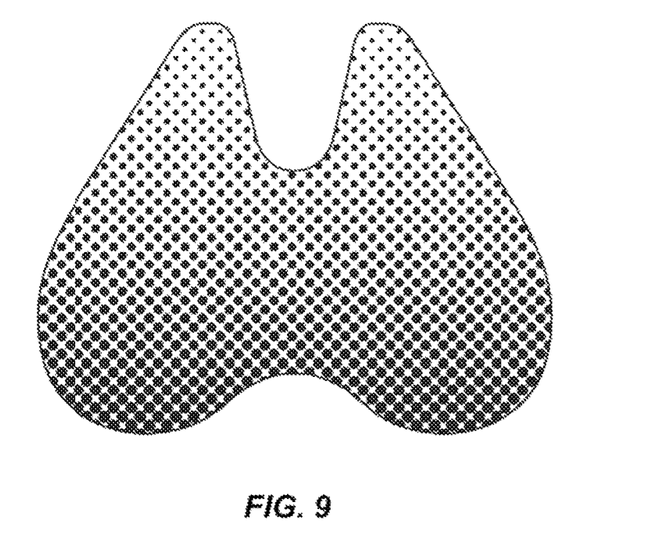
FIG. 9 is a front elevation schematic view of the lumbar-sacral implant shown in FIG. 1 depicting one embodiment of the varying durometer of the implant.
Figure 10:
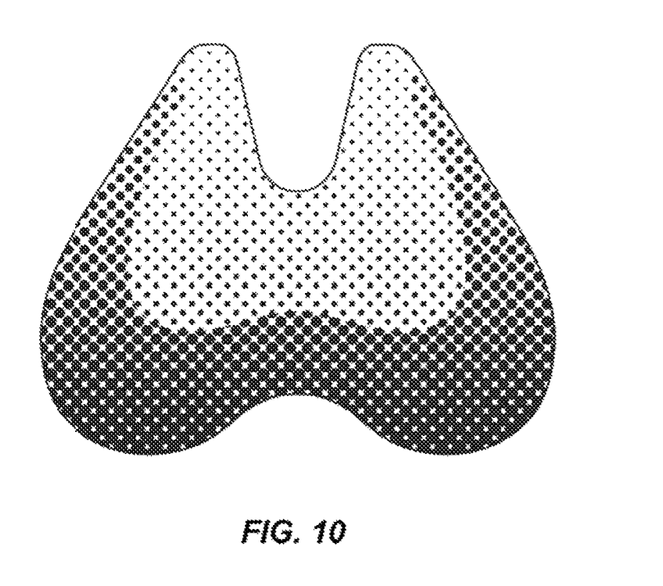
FIG. 10 is a front elevation schematic view of the lumbar-sacral implant shown in FIG. 1 depicting another embodiment of the varying durometer of the implant.

Implant 10 may be formed as a unitary body of a polymeric material having a gradual variation in the modulus of elasticity along and/or across its cross section. For example, the modulus may vary along the height of the body such that the upper portion of the body is more flexible than the lower portion of the body. See for example FIG. 9, which shows this arrangement schematically. Alternatively, the modulus may vary along the width of the body such that the outer lateral portions of the body are stiffer than the central portion of the body. The modulus may also vary along the width and height of the body such that the outer lateral portions and the lower portion of the body are stiffer than the central and upper portion of the body. See for example FIG. 10, which shows this arrangement schematically.

A material that may be formed into a product having a gradual variation in the modulus of elasticity, and the process for making the material, are disclosed in pending published U.S. Patent Application No. 2007/0050038, the entire contents of which are hereby expressly incorporated herein by reference. The material and process disclosed in the '038 Publication would allow the inferior portion of implant 10, or lower lobes 33a and 33b, to be relatively stiff, i.e. have a higher modulus of elasticity, so that fixation device 60 can firmly affix implant 10 to the spine while ensuring that the inferior portion, or lower lobes 33a and 33b, will not be pulled from fixation device 60 during flexion or other movement of the spine. Such pulling through of the implant is more likely if the inferior portion, or lower lobes 33a and 33b, were formed from a flexible material. Conversely, the material and process disclosed in the '038 Publication would allow the superior portion to be more elastic and flexible, i.e. have a lower modulus of elasticity. Having the superior portion be more flexible allows implant 10 to act as a shock absorber in extension while providing adequate stabilization to the L5/S1 level and allowing a more normal range of motion. In addition to having a gradual increasing of the modulus of elasticity from the top of implant 10 to the bottom of implant 10, the modulus of elasticity could vary from the surface of implant 10 to the inner core of implant 10 such that the inner core would have a lower modulus of elasticity than the surface. In this way, the inner core would be more flexible than the surface. In addition, the modulus of elasticity could vary from the top and central portions of implant 10 to the sides and bottom of implant 10 such that the sides and bottom portion of implant 10 would have a higher modulus of elasticity than the top and central portions. In this way, the sides and bottom would be stiffer than the top and central portions.

Figure 11:
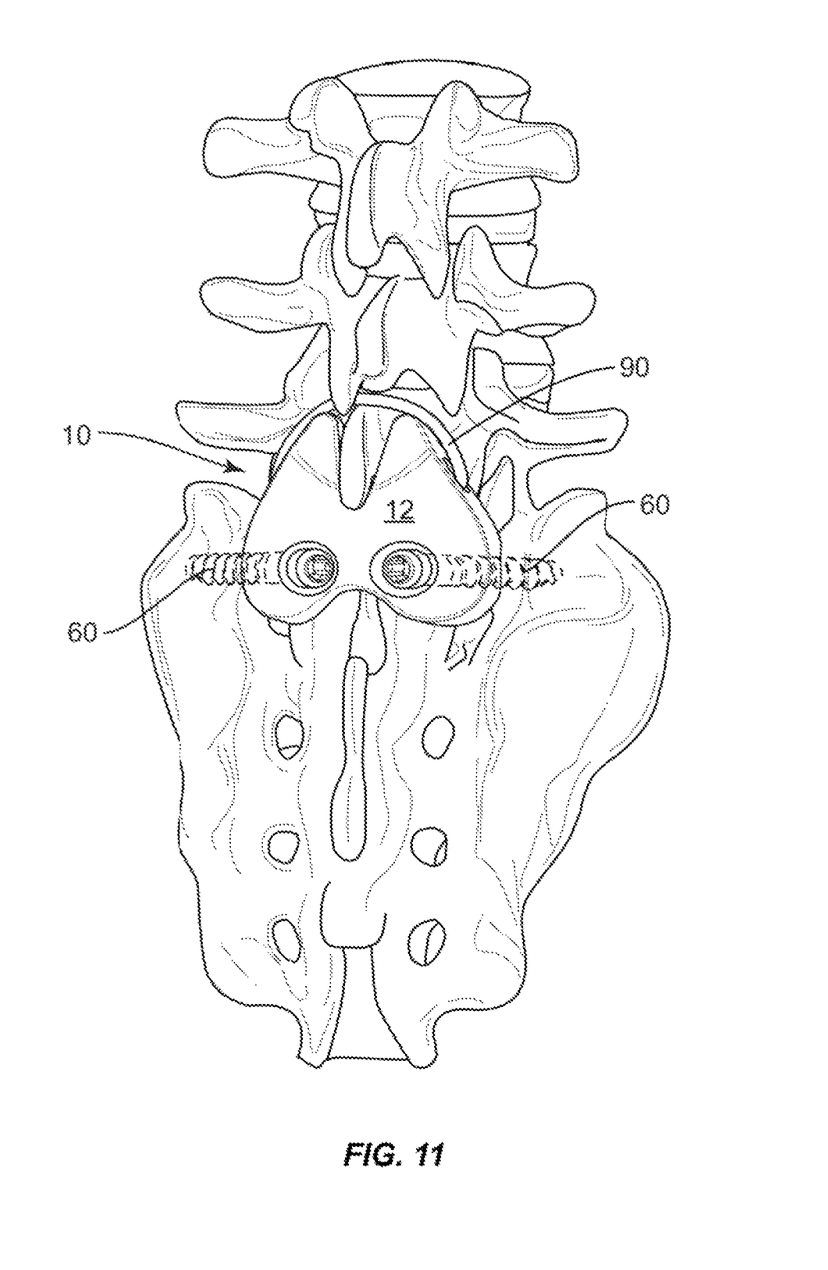
FIG. 11 is a front elevation view of the lumbar-sacral implant shown in FIG. 1 mounted on a spine.
Figure 12:
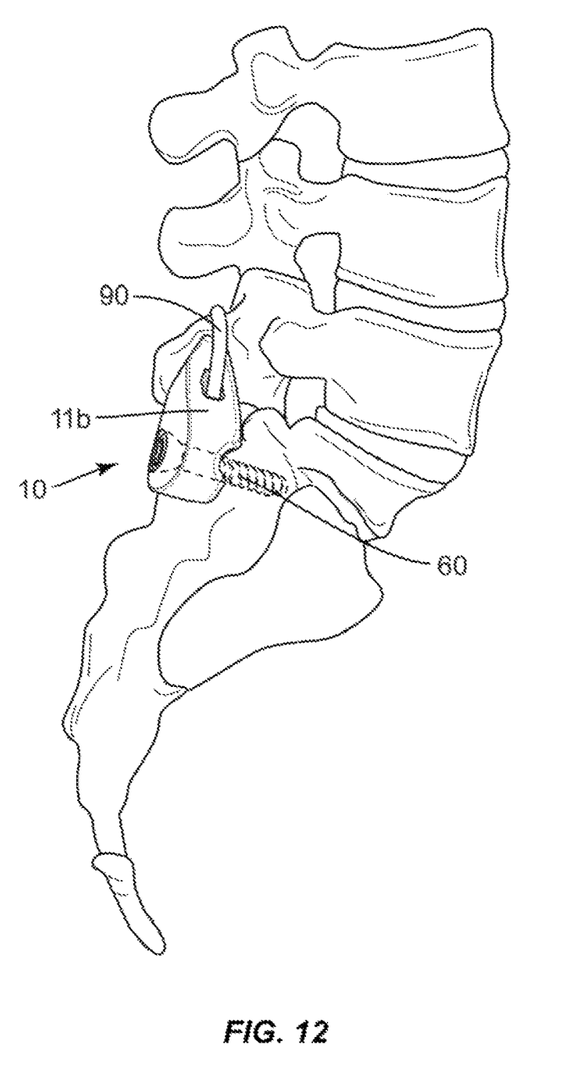
FIG. 12 is a side elevation view of the lumbar-sacral implant shown in FIG. 1 mounted on a spine.

Implant 10 may also define a curved passage 80 that extends between outer sidewalls 11a and 11b of implant 10. The curve of passage 80 may be defined by a radius of curvature of about 20 millimeters where the openings 85a and 85b to passage 80 are closer to the top of implant 10 than the nadir of passage 80. Openings 85a and 85b are generally perpendicular to outer sidewalls 11a and 11b. Other radii of curvature may also be used to define passage 80. The nadir of passage 80 may be substantially aligned in the sagittal plane with the bottom most portion of upper saddle bottom wall 22 and the uppermost portion of lower saddle top wall 32. A tether 90 may extend through passage 80. The curve of passage 80 facilitates tether 90 being threaded through passage 80 with a standard curved surgical needle. As shown in FIGS. 11 and 12, tether 90 may extend across the superior portion of the superior spinous process when implant 10 is located in the interspinous space. Tether 90 thus helps to maintain implant 10 in the proper position in the patient's anatomy during extension and flexion. It is to be understood that other fixation devices may be used instead of a tether 90. For example, a pin, rod, screw or other similar mechanical device may be used and would extend through upper saddle 20 and into the upper spinous process.

While various embodiments of the flexible interspinous process device have been described above, it should be understood that they have been presented by way of example only, and not limitation. Many modifications and variations will be apparent to the practitioner skilled in the art. The foregoing description of the flexible interspinous process device is not intended to be exhaustive or to limit the scope of the invention. It is intended that the scope of the invention be defined by the following claims and their equivalents.

What is claimed is:

1. A device, comprising:
a front face;
a rear face;
an upper body portion defining an upper saddle wherein the upper body portion has a first modulus of elasticity, the upper saddle is configured to receive and support a superior spinous process;
a lower body portion having a first sidewall and a second sidewall defining a lower saddle; the upper body portion separated from the lower body portion by an axial plane wherein the lower body portion has a second modulus of elasticity wherein the second modulus is greater than the first modulus, each sidewall flares out at angle between 25 degrees and 35 degrees such that contact with the inferior spinous process is avoided;
the lower body portion including a left lower lobe and a right lower lobe, each lobe being adjacent to an opposite side of the lower saddle;
a left sidewall, a right sidewall and a sagittal plane dividing the device into a left part and a right part, the left sidewall and the right sidewall each extending from the upper body portion to the lower body portion and extending away from the sagittal plane in a direction from the upper body portion to the lower body portion such that a first distance between the left sidewall and the right sidewall adjacent to the upper body portion is less than a second distance between the left sidewall and the right sidewall adjacent to the lower body portion; and
a left channel extending through the device in the left lower lobe and a right channel extending through the device in the right lower lobe.

2. The device of claim 1 wherein the device has a gradual variation in modulus such that the modulus gradually increases from the upper body portion to the lower body portion.

3. The device of claim 2 wherein the device has a gradual variation in modulus such that the modulus gradually increases from a central portion of the device to the left sidewall and the right sidewall.

4. The device of claim 1 wherein the device has a gradual variation in modulus such that the modulus gradually increases from a central portion of the device to the left sidewall and the right sidewall.

5. The device of claim 1 wherein the device includes a passageway extending between the left sidewall and the right sidewall.

6. The device of claim 5 wherein the passageway is curved.

7. The device of claim 6 wherein the curve of the passageway is configured to receive a curved surgical needle utilized to thread a tether through the passageway.

8. The device of claim 5 wherein the passageway is configured to receive a tether.

9. The device of claim 8 wherein the tether is configured to stabilize positioning of the device during flexion and extension.

10. A device, comprising: an upper body portion defining an upper saddle wherein the upper body portion has a first modulus of elasticity; and a lower body portion defining a lower saddle wherein the lower body portion has a second modulus of elasticity wherein the second modulus is greater than the first modulus, the lower saddle is defined by a first sidewall and a second sidewall, each sidewall flares out at angle between 25 degrees and 35 degrees such that contact with an inferior spinous process is avoided.

11. The device of claim 10 wherein the device has a gradual variation in modulus such that the modulus gradually increases from the upper body portion to the lower body portion.

12. The device of claim 11 wherein the device has a gradual variation in modulus such that the modulus gradually increases from a central portion of the device to a left sidewall and a right sidewall.

13. The device of claim 10 wherein the device has a gradual variation in modulus such that the modulus gradually increases from a central portion of the device to a left sidewall and a right sidewall.

14. A device, comprising:
a front face;
a rear face;
an upper body portion defining an upper saddle, the upper saddle configured to receive and support a superior spinous process;
a lower body portion defining a lower saddle; the upper body portion separated from the lower body portion by an axial plane; the lower body portion including a left lower lobe and a right lower lobe, each lobe being adjacent to an opposite side of the lower saddle;
a left sidewall, a right sidewall and a sagittal plane dividing the device into a left part and a right part, the left sidewall and the right sidewall each extending from the upper body portion to the lower body portion and extending away from the sagittal plane in a direction from the upper body portion to the lower body portion such that a first distance between the left sidewall and the right sidewall adjacent to the upper body portion is less than a second distance between the left sidewall and the right sidewall adjacent to the lower body portion, the left sidewall and the right sidewall of the lower body portion each flare out at angle between 25 degrees and 35 degrees such that contact with the inferior spinous process is avoided;
a central body portion disposed between the upper body portion and the lower body portion and between the left part and the right part; and
a left channel extending through the device in the left lower lobe and a right channel extending through the device in the right lower lobe, wherein a modulus of elasticity of the device gradually varies across the device.

15. The device of claim 14 wherein the modulus increases from the upper body portion to the lower body portion.

16. The device of claim 15 wherein the modulus decreases from the left sidewall to the central body portion.

17. The device of claim 15 wherein the modulus decreases from the right sidewall to the central body portion.

18. The device of claim 14 wherein the modulus decreases from the left sidewall to the central body portion.

19. The device of claim 14 wherein the modulus decreases from the right sidewall to the central body portion.

20. The device of claim 14 wherein the device includes an inner body portion between the front face and the rear face wherein the modulus decreases from the front face and the rear face to the inner body portion.

* * * * *